United States Patent
Verma et al.

(10) Patent No.: US 11,040,119 B2
(45) Date of Patent: Jun. 22, 2021

(54) COMPOSITIONS AND METHODS FOR ASSESSING NEUROMUSCULAR FUNCTION

(71) Applicant: Biogen MA Inc., Cambridge, MA (US)

(72) Inventors: Ajay Verma, Needham, MA (US); Jack Hoppin, Boston, MA (US)

(73) Assignee: Biogen MA Inc., Cambridge, MA (US)

( * ) Notice: Subject to any disclaimer, the term of this patent is extended or adjusted under 35 U.S.C. 154(b) by 661 days.

(21) Appl. No.: 14/774,510

(22) PCT Filed: Mar. 12, 2014

(86) PCT No.: PCT/US2014/024937
§ 371 (c)(1),
(2) Date: Sep. 10, 2015

(87) PCT Pub. No.: WO2014/151080
PCT Pub. Date: Sep. 25, 2014

(65) Prior Publication Data
US 2016/0030604 A1    Feb. 4, 2016

Related U.S. Application Data

(60) Provisional application No. 61/799,073, filed on Mar. 15, 2013.

(51) Int. Cl.
*A61K 51/04* (2006.01)
*A61B 5/00* (2006.01)
*G01N 33/60* (2006.01)
*G01N 33/68* (2006.01)

(52) U.S. Cl.
CPC ........ *A61K 51/0476* (2013.01); *A61B 5/4519* (2013.01); *A61B 5/4833* (2013.01); *G01N 33/60* (2013.01); *G01N 33/6896* (2013.01); *G01N 2800/2835* (2013.01)

(58) Field of Classification Search
None
See application file for complete search history.

(56) References Cited

U.S. PATENT DOCUMENTS

2011/0085969 A1* 4/2011 Rollo ................ A61K 51/0491
424/1.41

FOREIGN PATENT DOCUMENTS

WO    WO 2008/010227 A2    1/2008

OTHER PUBLICATIONS

Udelson et al. Predicting recovery of severe regional ventricular dysfunction. Comparison of resting scintigraphy with 201Tl and 99mTc-sestamibi. 1994 Circulation 89: 2552-2561. (Year: 1994).*
Cittanti et al. Technetium-99m sestamibi leg scintigraphy for non-invasive assessment of propionyl-L-carnitine induced changes in skeletal muscle metabolism. 1997 Eur. J. Nucl. Med. 24: 762-766. (Year: 1997).*
International Search Report and Written Opinion for International Application No. PCT/US2014/024937 dated Jul. 21, 2014.
International Preliminary Report on Patentability for for International Application No. PCT/US2014/024937 dated Sep. 24, 2015.
Arsos et al., (99m)Tc-sestamibi uptake in rat skeletal muscle and heart: physiological determinants and correlations. Physiol Res. 2009;58(1):21-8. Epub Jan. 17, 2008.
Brismar, In vivo analysis of intracellular thallium-201 accumulation in skeletal muscle of the rat. Acta Physiol Scand. Aug. 1991;142(4):475-80.
De Jong et al., Simultaneous (99m)Tc/(201)Tl dual-isotope SPET with Monte Carlo-based down-scatter correction. Eur J Nucl Med Mol Imaging. Aug. 2002;29(8):1063-71. Epub May 25, 2002.
Lastoria et al., Functional imaging of thymic disorders. Ann Med. Oct. 1999;31 Suppl 2:63-9.

* cited by examiner

*Primary Examiner* — Jennifer Lamberski
(74) *Attorney, Agent, or Firm* — Wolf, Greenfield & Sacks, P.C.

(57) ABSTRACT

The invention provides compositions and methods for evaluating neuromuscular function in a subject, e.g., a subject at risk for or suffering from a neuromuscular disorder.

19 Claims, 7 Drawing Sheets

Thallium                    Sestamibi

COMPOSITIONS AND METHODS FOR ASSESSING NEUROMUSCULAR FUNCTION

CROSS REFERENCE TO RELATED APPLICATIONS

This application is a national stage filing under 35 U.S.C. § 371 of International Patent Application Serial No. PCT/US2014/024937, filed Mar. 12, 2014, which claims the benefit of U.S. Provisional Application No. 61/799,073, filed Mar. 15, 2013, the contents of each of which are incorporated herein by reference in their entirety.

BACKGROUND

Neuromuscular diseases affect muscles and/or their nervous system control, and thus impact voluntary control of movements. As a result, muscles weaken and waste away. Routine functions such as walking, talking, swallowing and breathing become compromised. Some neuromuscular disorders, such as Spinal Muscular Atrophy (SMA) and Amyotrophic Lateral Sclerosis (ALS), carry a high rate of morbidity and mortality because of the current lack of therapies.

There is high demand for minimally invasive assays for the characterization of neuromuscular function for the early diagnosis of disease and monitoring of clinical status. Given the high interest in developing therapeutics for diseases like muscular dystrophy, SMA, and ALS, there is also a great demand by the pharmaceutical industry for convenient approaches that permit tracking of the action of novel therapeutics in neuromuscular disease. Such approaches would dramatically improve the efficiency of drug development efforts.

Current approaches for evaluating muscle disorders largely rely on electrophysiology assays, strength testing and muscle biopsies. These techniques are highly operator dependent, however, and need to be applied to individual muscles one at a time. Many muscles are in fact not readily accessible for these tests. The restrictions posed by currently available tests for muscle function have presented significant challenges for drug development and disease diagnosis. Thus, the need exists for improved methods to detect neuromuscular health and function.

SUMMARY OF THE INVENTION

The invention is based, at least in part, on the development of assays and methods for assessing skeletal muscle function and/or health in a subject. In embodiments, the assays and methods disclosed herein include evaluating an indicator of mitochondrial function or activity, alone or in combination with an indicator of ionic metabolism (e.g., plasma membrane ionic metabolism). In one embodiment, assays and methods have been developed that include the administration of an indicator of mitochondrial function or activity, e.g., $^{99m}$-Technetium-Sestamibi, and an indicator of ionic metabolism, e.g., $^{201}$Thallium-Chloride, in a subject in a way that allows for the simultaneous detection (or substantially simultaneous detection) of an accumulation of the indicator in skeletal muscle of the subject. The indicators can be administered in the presence or absence of a neuromuscular modulator (e.g., a neuromuscular stimulating agent, such as a cholinesterase inhibitor). The assays disclosed herein allow for detection of each indicator alone or in combination, also referred to herein, respectively, as "single" or "dual" detection or imaging. Single and dual detection of the agents enables the evaluation of multiple neuromuscular processes in an efficient, quantitative and qualitative manner.

Therefore, provided herein, at least in part, are efficient, quantitative assays and methods, as well as compositions and kits for assessing a neuromuscular status in a subject. The invention can be used, and methods are provided herein, for one or more of: (i) diagnosing, prognosing and/or evaluating, a subject (e.g., a subject having a neuronal and/or skeletal muscular disorders or conditions, including but not limited to, a muscle disorder, a motor neuron disease (e.g., Spinal Muscular Atrophy (SMA), Amyotrophic Lateral Sclerosis (ALS), neuropathy, myasthenia gravis, toxic syndromes, traumatic nerve injury, or a metabolic muscle disease); (ii) evaluating responsiveness to, or monitoring, a therapy; (iii) identifying a patient as being stable, showing improvement or showing disease progression; (iv) stratifying a subject; and/or (vi) more effectively monitoring, treating, or preventing a neuronal and/or muscular disorders or conditions.

Accordingly, in one aspect, the invention features an assay, or a method, for evaluating a neuromuscular status in a subject. The method includes:
administering to the subject a first and a second detectable agent, wherein:
the first detectable agent is an indicator of mitochondrial function or activity, and the second detectable agent is an indicator of ionic metabolism, e.g., plasma membrane ionic metabolism; and
detecting the first and second detectable agents disposed in a skeletal muscle cell or tissue in the subject,
wherein the first and second agents are administered at a time and/or in an amount sufficient for each agent (or both agents) to be detected in the subject within a detection interval; and optionally, wherein a change in one or more of the first detectable agent, the second detectable agent, or both, relative to a reference value, is indicative of neuromuscular status.

In certain embodiments, the assay, or method, further includes providing to the subject a neuromuscular modulation, e.g., a neuromuscular stimulation, in an amount or level such that one or more processes (e.g., physiological processes) in the skeletal muscle or tissue are modulated, e.g., stimulated.

In a related aspect, the invention features an assay, or a method, for evaluating a neuromuscular status in a subject. The method includes one, two, or three of the following:
(i) administering to the subject a first detectable agent that is an indicator of mitochondrial function or activity at a time and/or in an amount sufficient to be detected in the subject;
(ii) administering to the subject a second detectable agent that is an indicator of ionic metabolism, e.g., plasma membrane ionic metabolism, at a time and/or in an amount sufficient to be detected in the subject; and/or
(iii) providing to the subject a neuromuscular modulation, e.g., a neuromuscular stimulation, in an amount or level such that one or more processes (e.g., physiological processes) in the skeletal muscle or tissue are modulated, e.g., stimulated; and
detecting the first and/or the second detectable agents disposed in a skeletal muscle cell or tissue in the subject,
optionally, wherein a change in one or more of the first detectable agent, the second detectable agent, or both, in the presence or absence of neuromuscular modulation, relative to a reference value is indicative of neuromuscular status.

In certain embodiments, the first detectable agent is administered to the subject in the presence or absence of the neuromuscular modulation. In other embodiments, the second detectable agent is administered to the subject in the presence or absence of the neuromuscular modulation. In another embodiment, the first and second detectable agents are administered to the subject. In yet another embodiment, the first and second detectable agents are administered to the subject in the presence or absence of neuromuscular modulation. In embodiments where the first and second detectable agents are administered to the subject, such administration can be effected at a time and/or in an amount sufficient for each agent to be detected in the subject within a detection interval.

Additional features and embodiments of the methods and assays described herein include one or more of the following:

First and Second Detectable Agents

In embodiments of the aforesaid methods and assays, one or both of the first and second detectable agents is, or comprises, a detectable moiety, e.g., a radioactive moiety (e.g., a radionuclide). Exemplary radionuclides that can be used include, but are not limited to, a beta- or gamma-ray emitter, or a combination thereof.

In one embodiment, the first and second detectable agents each are, or comprise, a radionuclide that is a gamma-ray emitter, e.g., a radionuclide that emits energies above 100 keV and a wavelength of less than 10 picometers. Exemplary radionuclides that can be used as detectable moieties, include, but are not limited to, technetium (e.g., $^{99m}$Tc), indium (e.g., $^{111}$In), cobalt (e.g., $^{57}$Co), chromium (e.g., $^{51}$Cr), thallium (e.g., $^{201}$Tl), gallium (e.g., $^{67}$Ga), iodine (e.g., $^{123}$I, $^{125}$I, $^{131}$I) lutetium (e.g., $^{177}$Lu), and samarium (e.g., $^{153}$Sm). Any combination of the aforesaid radionuclides, or nuclear isomers thereof, can be used as a first and second detectable moiety. In embodiments, the combinations are suitable for dual-isotope detection or imaging, e.g., SPECT imaging. Exemplary combinations include, but are not limited to, technetium (e.g., $^{99m}$Tc) and thallium (e.g., $^{201}$Tl), indium (e.g., $^{111}$In) and lutetium (e.g., $^{177}$Lu), technetium (e.g., $^{99m}$Tc) and indium (e.g., $^{111}$In), and technetium (e.g., $^{99m}$Tc) and iodine (e.g., $^{123}$I), or nuclear isomers thereof.

In certain embodiments, the radionuclides are appended, e.g., covalently or non-covalently, to a moiety or carrier. In embodiments, the radionuclide is present in a molecular cage or a chelator. In other embodiments, the radionuclide is appended to a targeting moiety, e.g., a mitochondrial targeting moiety, or an ion channel- or pump-targeting moiety, or a moiety having an affinity (e.g., electrostatic affinity) to the mitochondrial or an ion channel or pump.

In one embodiment, the first detectable agent is capable of distributing and/or localizing to the mitochondria in the skeletal muscle cell or tissue in the subject. For example, the first detectable agent can be, or can include, a lipophilic and/or a positively charged agent. Typically, the detectable agent can pass through a cell membrane (e.g., it is membrane permeable) and accumulates in an electronegative environment, such as the mitochondria (e.g., the muscle mitochondria).

In one embodiment, the first detectable agent is, or comprises, technetium or a nuclear isomer of technetium (e.g., technetium-99m). The radionuclide can be disposed in a molecular cage, e.g., a chelator. Exemplary chelators include, but are not limited to, methoxyisobutylisonitrile (MIBI), teboroxime and tetrofosmin (two 1,2-bis[di-(2-ethoxyethyl)phosphino]ethane ligands). In one embodiment, the first detectable agent is, or comprises, $^{99m}$-Tc-Sestamibi.

In another embodiment, the first detectable agent is, or comprises, a fatty acid or a modified fatty acid. In one embodiment, the fatty acid or the modified fatty acid is associated (e.g., covalently or non-covalently) to a radionuclide, e.g., a radionuclide as described herein (e.g., technetium (e.g., technetium-99m). Exemplary fatty acids can be saturated, e.g., chosen from caprylic acid, capric acid, lauric acid, myristic acid, palmitic acid, stearic acid, arachidic acid, behenic acid, lignocercic acid, or cerotic acid; or unsaturated, e.g., chosen from myristoleic acid, palmitoleic acid, sapienic acid, oleic acid, elaidic acid, vaccenic acid, linoleic acid, linoelaidic acid, alpha-linolenic acid, arachidonic acid, eicosapentaenoic acid, erucic acid, or docosahexaenoic acid; or a modified form thereof.

In other embodiments, the second detectable agent distributes and/or localizes to the skeletal muscle cell or tissue, e.g., a perfused muscle cell or tissue. The level, e.g., amount, of the second detectable agent can be indicative of tissue perfusion and/or a function of one or more of: a sodium-potassium pump, an ion channel or an ion carrier in the skeletal muscle cell or tissue. In one embodiment, the second detectable agent is, or comprises, a potassium analogue, e.g., is a monovalent cation having an ionic radius, charge, and/or charge distribution similar to that of $K^+$. The potassium analogue can be a radionuclide, and thus capable of being detected by the methods described herein. Exemplary potassium analogues that can be used as indicators of plasma membrane function include, but are not limited to, cesium ions (e.g., $^{127}$Cs, $^{129}$Cs), rubidium ions (e.g., $^{81}$Rb, $^{82}$Rb), thallium ions (e.g., $^{199}$Tl, $^{201}$Tl), and ammonium ions (e.g., $^{13}$N ammonium ions), or salts thereof. The potassium analogues can be in salt form. In certain embodiments, the potassium analogues are chosen from $Tl^+$, $Cs^+$, or $Rb^+$, or salts thereof. In one embodiment, the second detectable agent is, or comprises, a thallium isotope, e.g., $^{201}$Tl. For example, the second detectable agent can be $^{201}$Tl—Cl.

Neuromuscular Modulation

In other embodiments, the aforesaid methods and assays further include subjecting the subject to a neuromuscular modulation. In one embodiment, the subject is exposed to neuromuscular stimulation. In other embodiments, the subject is exposed to neuromuscular inhibition. The neuromuscular modulation can be effected systemically or locally (e.g., in a pre-selected skeletal muscle or region) in the subject. In certain embodiments, the subject is evaluated in the presence or absence of neuromuscular modulation. For example, detection can be carried out in pre-selected skeletal muscle or tissue exposed to a neuromuscular modulation, relative to the same or a different skeletal muscle or tissue, prior to, after, or not exposed to, the neuromuscular modulation. In exemplary embodiments, the subject is evaluated under exercise or other stress condition, relative to a subject in a rest or unstimulated state. In other embodiments, the subject is placed under stress, e.g., electrical stimulation or pharmacological stimulation, of one or more muscles to activate locally or regionally pre-selected muscles. In such embodiments, a reference value can be obtained from a control subject, or a tissue from the same subject which is not exposed to the neuromuscular modulation.

Neuromuscular stimulation can include one or more of: an electrical stimulation, stimulation by a physical activity, or by administration of a neuromuscular stimulating agent. In some embodiments, the neuromuscular stimulation is, or comprises, administration (e.g., systemic or local administration) of a neuromuscular stimulating agent, e.g., an agent that enhances or activates neuromuscular activity pre-synaptically, post-synaptically, or both. In one embodiment, the neuromuscular stimulating agent is a cholinesterase inhibitor, e.g., an acetylcholinesterase inhibitor. For example, a cholinesterase inhibitor chosen from one or more of ambenonium, ambenonium chloride, demecarium, demecarium bromide, echothiophate iodide, edrophonium, edrophonium chloride, neostigmine, neostigmine bromide, neostigmine methylsulfate, physostigmine, physostigmine salicylate, pyridostigmine, or pyridostigmine bromide. In one embodiment, the neuromuscular stimulating agent is an acetylcholinesterase inhibitor, e.g., edrophonium or edrophonium chloride.

In other embodiments, the subject is exposed to neuromuscular inhibition. Neuromuscular inhibition can be effected by administration (e.g., local or systemic administration) of an agent that reduces or inhibits neuromuscular activity pre-synaptically, post-synaptically, or both. In some embodiments, the agent is a neuromuscular blocking agent (e.g., a toxin (e.g., alpha-bungarotoxin)) or a ganglionic blocking drug (e.g., dicholine esters (e.g., succinylcholine), benzylisoquinolines (d-tubocurarine, atracurium, doxacurium, mivacurium) and pipecuronium, rocuronium, vecuronium), hexamethonium, trimethaphan, and mecamylamine. In other embodiments, the neuromuscular blocking agent is an anesthetic agent, including but not limited to, a ketamine, isofluorane; an opioid analgesic such as alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, and tramadol; a nonopioid analgesic such as apazone, etodolac, diphenpyramide, indomethacine, meclofenamate, mefenamic acid, oxaprozin, phenylbutazone, piroxicam, and tolmetin.

Neuromuscular modulation in the subject can occur at any time prior to, concurrently, or after administration of one or both of the first and second detectable agents. In one embodiment, the neuromuscular modulation occurs prior to administration of one or both of the first and second detectable agents, e.g., occurs 5 hours or less, 4 hours or less, 3 hours or less, 2 hours of less, 1 hour or less, or 30 minutes or less, prior to administration of one or both of the first and second detectable agents. In other embodiments, the neuromuscular modulation occurs after administration of one or both of the first and second detectable agents, e.g., occurs 5 hours or less, 4 hours or less, 3 hours or less, 2 hours of less, 1 hour or less, or 30 minutes or less, after administration of one or both of the first and second detectable agents. In yet other embodiments, neuromuscular modulation occurs concurrently with administration of one or both of the first and second detectable agents.

Detection

In embodiments of the aforesaid methods and assays, the first and/or second detectable agents are administered at a time and/or dose sufficient for each agent (or both agents) to be detected within a detection interval. In one embodiment, the detection interval allows for the single detection of a first or a second detectable agent, or the dual detection of both first and second detectable agents. The dual detection can be simultaneous, substantially simultaneous (e.g., within minutes apart), or sequential (e.g., in any order of first or second agent). In one embodiment, the detection interval comprises the simultaneous detection of the first and second agents. In embodiments where dual detection is desired, the detection interval can occur within hours from the detection of one agent (e.g., a first or second agent) relative to the detection of the other agent. In one embodiment, the detection interval occurs within 12 hours or less, 10 hours or less, 8 hours or less, 7 hours or less, 6 hours or less, 5 hours or less, 4 hours or less, 3 hours or less, 2 hours or less, or 1 hours or less, from the detection of one agent (e.g., a first or second agent) to the detection of the other agent. In other embodiments, one or both of the first and second detectable agents are administered at less than 1 hour, or 1, 2, 3, 4, 5, 6, 7, 8, 9, 10, 11, 12 or more hours before detection.

Single or dual detection can be carried out, e.g., acquired, using one or more of Single Photon Emission Computerized Tomography (SPECT) imaging, Positron Emission Tomography (PET), Magnetic Resonance Imaging (MRI) or scintigraphy. In certain embodiments, a single imaging method is used for single or dual detection of the agents.

In one embodiment, the single or dual detection is acquired using SPECT imaging. For example, the detection of the first and second detectable agents can comprise a dual-radionuclide evaluation. In an exemplary embodiment, the first detectable agent emits an energy level that is different from the energy emitted by the second detectable agent. Differential detection of the first and second agents can be carried out by setting multiple energy windows during image acquisition, e.g., by SPECT imaging. For example, a first detection window that is specific for the first detectable agent (e.g., the radiation signal from the first detectable agent) is distinguishable from a second detection window that is specific for the second detectable agent (e.g., the radiation signal from the second detectable agent). In embodiments, the detection interval comprises evaluation of a signal (e.g., radiation signal) that is specific for the first agent and a signal (e.g., radiation signal) that is specific for the second agent.

In certain embodiments, the detection step includes acquiring an image of the whole body of the subject. In other embodiments, the detection step includes acquiring an image of one or more tissues of the subject, e.g., a skeletal muscle or tissue in the subject. In embodiments, the one or more tissues are chosen from one of more of limbs, legs, lower legs, arms, shoulders, or back. Exemplary muscles or tissues that can be evaluated include, but are not limited to, a lateral muscle, a medial muscle, a sartorious muscle, a vastus muscle (e.g., a vastus medialis, a vastus lateralis), a rectus, and a femoral bicep.

The first and/or second detectable agent can be detected in the skeletal muscle or tissue qualitatively or quantitatively. In certain embodiments, the amount of the detected agent is quantified. It can be evaluated as an absolute number or as a ratio, e.g., a ratio of first detectable agent in relation to the second detectable agent, or vice versa; or a ratio of a first or second detectable agent relative to the initial amount or dose of said agent administered to the subject (e.g., a percentage of the injected dose). In one exemplary embodiment shown in FIG. 7, a ratio of $^{201}$Tl to $^{99m}$Tc-Sestamibi in skeletal muscle was detected in a subject (with or without treatment with edrophonium).

Neuromuscular Status

In some embodiments, the methods or assays provided herein can be used to evaluate neuromuscular status. The neuromuscular status can comprise at least one parameter indicative of muscle physiology (e.g., a physiological parameter in a skeletal muscle or tissue) including one or more of activity, metabolism, integrity, or health of a motor nerve cell or tissue, or a skeletal muscle cell or tissue, or both. In certain embodiments, the parameter in the skeletal muscle cell or tissue is chosen from one or more of: uptake of a detectable agent; a change in membrane ionic metabolism; modulation of activity of an ion channel, a carrier or a pump; or modulation of mitochondrial function.

In some embodiments, a change in the first or a second detectable agent is detected. In another embodiment, a change of a first agent in relation to the second agent is detected. In yet another embodiment, a change of a second agent in relation to the first agent is detected. In certain embodiments, a change in the level of detection (e.g., amount) of the first or the second agent over a time period (e.g., first and second time periods) is evaluated. For example, a change can be evaluated in one or more of: an asymptomatic subject, e.g., to provide a diagnosis; before, during or after a therapy, e.g., to determine or monitor the efficacy of a treatment; or at one or more time intervals of a disease, e.g., to determine or monitor disease progression.

In one embodiment, a decrease in the level of detection (e.g., amount) of a first and/or second detectable agent in relation to a reference value is indicative of worsening of neuromuscular status.

In other embodiments, an increase in the level of detection (e.g., amount) of a first and/or second detectable agent in relation to a reference value is indicative of an improved neuromuscular status.

In certain embodiments, the amount of the one or both of the first or second detectable agents is compared to a reference value of the first or the second detectable agents, e.g., a historical reference.

The reference value can be obtained from a control subject or group of subjects (e.g., a healthy subject or group of subjects), or from the same subject at different time intervals, e.g., at different stages of the disease, or before or after administration of a therapy or treatment (e.g., experimental treatment). Alternatively, the reference value can be obtained from two different tissues or regions of the subject (e.g., a stimulated tissue or region compared to an unstimulated tissue or region). In yet other embodiments, the reference value is obtained by comparing a read-out of a one detectable agent relative to the other (e.g., a first vs. a second detection read-out).

In some embodiments, the subject is a human, e.g., an adult or a child, a male or a female. In embodiments, the subject has a skeletal muscle disorder, a motor neuron disease (e.g., SMA, ALS), a neuropathy, myasthenia gravis, a toxic syndrome, a traumatic nerve injury, or a metabolic muscle disease. In one embodiment, the subject is a patient being considered for a treatment (e.g., a new treatment or a change in treatment). In other embodiments, the subject is undergoing a treatment. In other embodiments, the subject has not been diagnosed with a disorder, e.g., a disorder as described herein. In one embodiment, the subject may be experiencing one or more symptoms (e.g., muscle weakening or decreased coordination) but has not been diagnosed with a disorder, e.g., a disorder as described herein. In yet other embodiments, the subject is asymptomatic.

In certain embodiments a determination of a lower level (e.g., amount) of one or both of the first or second detectable agent as compared to the reference value is indicative of skeletal muscle disorder, a motor neuron disease (e.g., SMA, ALS), neuropathy, myasthenia gravis, toxic syndromes, traumatic nerve injury, or a metabolic muscle disease.

Agent Administration:

The first and second detectable agents can be administered to the subject concurrently or simultaneously. In one embodiment, the first and second detectable agents are premixed in the same vial.

In other embodiments, the first and second detectable agents are administered sequentially. For example, administration of the first and second detectable agents can overlap in part with each other. In other embodiments, the first detectable agent is administered before initiating administration of the second detectable agent. In yet other embodiments, the second detectable agent is administered before initiating administration of the second detectable agent. In other embodiments, administration of the first detectable agent continues after cessation of administration of the second detectable agent, or administration of the second detectable agent continues after cessation of administration of the first detectable agent.

One or both of the first and second detectable agents can be administered parenterally, e.g., wherein the parenteral administration is selected from intravenous, intramuscular, subcutaneous, intradermal, intracardiac, intraocular, intrathecal, intraarticular or epidural administration. In one embodiment, the first or the second detectable agent (or both agents) is/are administered intravenously.

Compositions

In another aspect, the invention features a composition for evaluating neuromuscular status in a subject, comprising a first and second detectable agent, wherein the first detectable agent is the first detectable agent is an indicator of mitochondrial function or activity, and the second detectable agent is an indicator of plasma membrane ionic metabolism. The composition can be suitable for parenteral administration, e.g., intravenous administration.

In embodiments, the first detectable agent of the composition is or comprises a lipophilic and/or positively charged agent, e.g., as described herein.

In other embodiments, the second detectable agent is or comprises an analog of potassium, e.g., an analog of potassium as described herein.

The composition can further comprise a pharmaceutically acceptable carrier.

In yet other embodiments, the composition further comprises a neuromuscular modulator, e.g., a neuromuscular stimulating agent, e.g., a neuromuscular stimulating agent as described herein.

Kits

In another aspect, the invention features a kit comprising:
a first and second detectable agent, wherein the first detectable agent is an indicator of mitochondrial function or activity, and
the second detectable agent is an indicator of plasma membrane ionic metabolism; and
instructions for administration of the first and second detectable agents to a subject at a time and in an amount sufficient for each agent to be detected in the subject's body simultaneously.

In embodiments, the kit can further comprising a neuromuscular stimulating agent.

In embodiments of the kit, the first and second detectable agents are disposed in the same vial/receptacle. In another embodiment, the first and second detectable agent and neuromuscular stimulating agent are disposed in the same vial/receptacle.

Neuromuscular Status Value

A determination of neuromuscular status (e.g., one or more parameters of neuromuscular physiology described herein) in a subject can be used to provide or acquire a value of neuromuscular status (also referred to herein as "neuromuscular status value"). The neuromuscular status value can be qualitatively or quantitative. In certain embodiments, the neuromuscular status value is quantified. It can be provided as an absolute number or as a ratio, e.g., a ratio of first detectable agent in relation to the second detectable agent, or vice versa; or a ratio of a first or second detectable agent relative to the initial amount or dose of said agent administered to the subject (e.g., a percentage of the injected dose).

In one embodiment, an increase in the neuromuscular status value (e.g., an increase in the level or amount of a first or second detectable agent, or both), relative to a specified or reference value (e.g., a baseline or prior value for the subject, or an average or median value for a patient population), is indicative of a better or improved diagnosis or prognosis (e.g., decreased disease progression), in the subject. Alternatively, a decrease in the neuromuscular status value (e.g., a decrease in the level or amount of a first or second detectable agent, or both), relative to a specified or reference value (e.g., a baseline or prior value for the subject, or an average or median value for a patient population), is indicative of a poorer diagnosis or prognosis (e.g., disease progression or worsening of symptoms and/or disability), in the subject.

A neuromuscular status value can be used in methods for one or more of: (i) diagnosing, prognosing and/or evaluating, a subject (e.g., a subject having a neuronal and/or skeletal muscular disorders or conditions, including but not limited to, a muscle disorder and a motor neuron disease (e.g., SMA, ALS, neuropathy, myasthenia gravis, toxic syndromes, traumatic nerve injury, or a metabolic muscle disease); (ii) evaluating responsiveness to, or monitoring, a therapy; (iii) identifying a patient as being stable, showing improvement or showing disease progression; (iv) to stratify a subject; and/or (vi) more effectively monitoring, treating, or preventing a neuronal and/or muscular disorders or conditions.

Accordingly, in another aspect, the invention features a method for evaluating a subject. The method includes acquiring a neuromuscular status value (e.g., a neuromuscular status value as described herein) in the subject (e.g., a patient, a patient group or a patient population) having a muscle disorder or a motor neuron disease (e.g., SMA, ALS, neuropathy, myasthenia gravis, toxic syndromes, traumatic nerve injury, or a metabolic muscle disease), or at risk of developing the muscle disorder or a motor neuron disease.

In some embodiments, responsive to a determination of said neuromuscular status value, the method further includes one or more of the following:

(i) diagnosing and/or prognosing the subject as having the muscle disorder or the motor neuron disease;

(ii) identifying the subject as being in need of a therapy, (e.g., a first therapy, a second or subsequent (alternative) therapy);

(iii) identifying the subject as having an increased or a decreased response to a therapy, (e.g., a first therapy or a second (alternative) therapy);

(iv) monitoring disease progression in the subject (e.g., identifying the subject as being stable or showing an improvement in one or more abilities or function, or showing a decline in one or more abilities or function); and/or (v) administering a therapy, e.g., a first therapy or a second (alternative therapy) to the subject.

In one embodiment, one or more of (i)-(v) are effected in response to the neuromuscular status value. A change (e.g., an increased or a decrease) in the neuromuscular status value relative to a specified or reference value indicates one or more of: identifies the subject as being in need of the therapy; identifies the subject as having an increased or decreased response to the therapy; determines the treatment to be used; and/or determines or predicts the time course of the disease (e.g., the progression of the disease).

In another aspect, the invention features a method of treating or preventing a muscle disorder or a motor neuron disease (e.g., SMA, ALS, neuropathy, myasthenia gravis, toxic syndromes, traumatic nerve injury, or a metabolic muscle disease) in a subject (e.g., a patient, a patient group or a patient population) having the disease or disorder, or at risk of developing the disease or disorder. The method includes acquiring a neuromuscular status value, and responsive to a determination of the value of the neuromuscular status value, performing one, two or more of:

administering a therapy;

administering an altered dosing of a therapy;

administering or altering the schedule or time course of a therapy; or administering an alternative therapy, thereby treating or preventing the muscle disorder or a motor neuron disease in the subject.

Timing of Assessment

In one embodiment, the methods described herein include comparing the neuromuscular status value to a specified value (e.g., a reference value as described herein). A value can be analyzed at any stage of treatment, for example, prior to, during, or after terminating, administration of the therapy, to thereby determine appropriate dosage(s) and therapy (e.g., amount per treatment or frequency of treatments) for prophylactic or therapeutic treatment of the subject. In certain embodiments, the methods include the step of acquiring the neuromuscular status value from the subject, prior to, or after, administering the therapy, to the subject.

In one embodiment, the disease progression value is assessed at pre-determined intervals, e.g., a first point in time and at least at a subsequent point in time. In certain embodiments, the values are obtained at least three, four, five, six, or twelve months apart.

Reports

The methods, systems, and/or kits described herein can further include providing or generating, and/or transmitting information, e.g., a report, containing data of the evaluation or treatment determined by the methods, and/or kits as described herein. In one embodiment, the disease progression value is memorialized. The value or information can be transmitted to a report-receiving party or entity (e.g., a patient, a health care provider, a diagnostic provider, and/or a regulatory agency, e.g., the FDA), or otherwise submitting information about the methods and kits disclosed herein to another party. The method can relate to compliance with a regulatory requirement, e.g., a pre- or post approval requirement of a regulatory agency, e.g., the FDA. In one embodiment, the report-receiving party or entity can determine if a predetermined requirement or reference value is met by the data, and, optionally, a response from the report-receiving entity or party is received, e.g., by a physician, patient, diagnostic provider.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DETAILED DESCRIPTION

Figure 1:
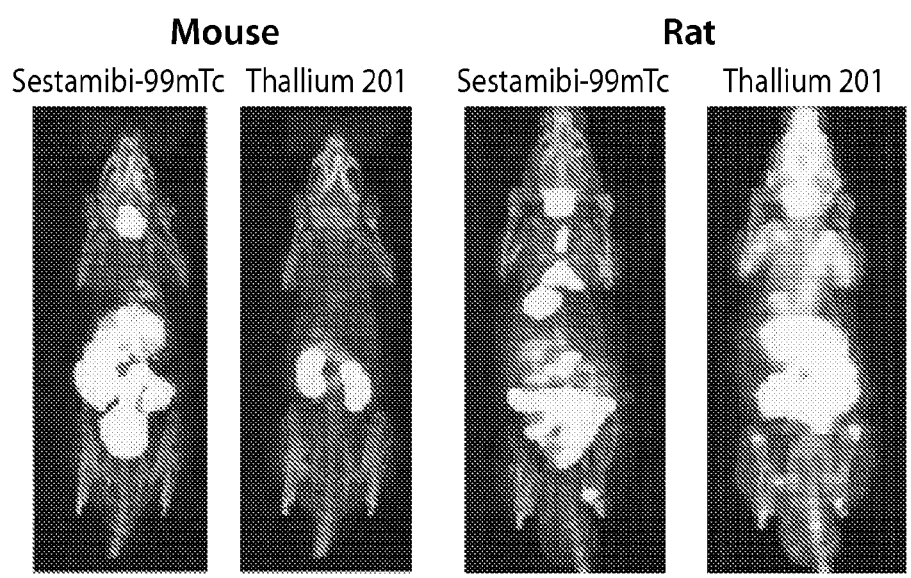
FIG. 1 depicts exemplary images showing simultaneous uptake of $^{99m}$Tc-Sestamibi and $^{201}$Tl—Cl in a single mouse and a single rat as viewed through distinct, isotope-specific imaging windows.

The invention is based, at least in part, on the development of assays for assessing skeletal muscle function and/or health in a subject, by evaluating an indicator of mitochondrial function or activity, alone or in combination with an indicator of ionic metabolism (e.g., plasma membrane ionic metabolism). In one embodiment, assays have been developed that include the administration of an indicator of mitochondrial function or activity, e.g., $^{99m}$-Technetium-Sestamibi, and an indicator of ionic metabolism, e.g., $^{201}$Thallium-Chloride, in a way that allows for the simultaneous detection (or substantially simultaneous detection, e.g., detection within minutes) of accumulation of the indicator in skeletal muscle. In embodiments, the indicators are administered in the presence or absence of a neuromuscular modulator, e.g., a neuromuscular stimulating agent, such as an acetylcholinesterase inhibitor. The assays disclosed herein allow for detection of each indicator alone or in combination. Single and dual detection of the agents, as well as a change in one indicator relative to the other (e.g., detection of increased or decreased uptake in a skeletal muscle or tissue), enables the ability to evaluate multiple neuromuscular processes in an efficient, quantitative and qualitative assay. Therefore, provided herein are efficient, quantitative assays and methods, as well as compositions and kits for assessing the neuromuscular status in a subject, which can be useful for, e.g., diagnosis, staging, and/or treating neuronal and/or muscular disorders or conditions.

Definitions

For convenience, before further description of the present invention, certain terms employed in the specification, examples and appended claims are defined here. Other terms are defined as they appear in the specification.

The singular forms "a", "an", and "the" include plural references unless the context clearly dictates otherwise.

"Acquire" or "acquiring" as the terms are used herein, refer to obtaining possession of, determining, or evaluating, a value, e.g., a numerical value, by "directly acquiring" or "indirectly acquiring" the value. "Directly acquiring" means performing a process (e.g., performing a test, e.g., a assay or test as described herein) to obtain the value. "Indirectly acquiring" refers to receiving the value from another party or source (e.g., a third party clinician or health professional that directly acquired the value).

"Neuromuscular status" refers to an indication of one or more of an activity, integrity, or health of a motor nerve cell or tissue, or a skeletal muscle cell or tissue, or both. In embodiments, a parameter of neuromuscular status is chosen from one or more of: uptake of a detectable agent by a skeletal muscle cell or tissue; plasma membrane ionic metabolism; modulation of activity of an ion channel, a carrier or a pump; mitochondrial function or activity; or tissue viability and/or bioenergetic status.

Any determination of neuromuscular status in a subject can be used to provide or acquire a value of neuromuscular status (also referred to herein as "neuromuscular status value"). The neuromuscular status value can be qualitatively or quantitative. When quantified, the neuromuscular status value can be provided as an absolute number or as a ratio, e.g., a ratio of first detectable agent in relation to the second detectable agent, or vice versa; or a ratio of a first or second detectable agent relative to the initial amount or dose of said agent administered to the subject (e.g., a percentage of the injected dose).

The terms "subject" or "patient", as used herein refer to an individual who requires detection and/or assessment of neuromuscular function. In some embodiments, a subject is at risk for or suffering from a neuromuscular disease, disorder or condition. The term "subject" or "patient" includes, but is not limited to, animals, e.g., mouse, rat, human. In some embodiments, the subject is a human, e.g., an adult or a child, male or female. In embodiments, the subject has a skeletal muscle disorder, a motor neuron disease (e.g., SMA, ALS), neuropathy, myasthenia gravis, toxic syndromes, traumatic nerve injury, or a metabolic muscle disease. In one embodiment, the subject has not been diagnosed with a disorder, e.g., a disorder as described herein. In one embodiment, the subject may be experiencing one or more symptoms (e.g., muscle weakening or decreased coordination) but has not been diagnosed with a disorder, e.g., a disorder as described herein. In yet other embodiments, the subject is asymptomatic.

The term "target tissue," as used herein generally refers to any tissue in the body of any subject, including the human body that comprises all the organs, structures and other contents. Specifically, a tissue is any substance made up of cells that perform a similar function within an organism. For example, tissue may refer to any epithelial tissue, connective tissue, muscle tissue, such as cardiac muscle, smooth muscle, and skeletal muscle, and any nervous tissue, such as tissue within the brain, spinal cord, and/or peripheral nervous system.

A disease or disorder is "treated," "inhibited" or "reduced," if at least one symptom of the disease is reduced, alleviated, terminated, slowed, or prevented.

Headings, including alphabetical or numerical headings, are merely for ease of understanding and reading and, absent express indication to the contrary, do not impose temporal order of a hierarchy of preferences.

Various aspects of the invention are described in further detail below. Additional definitions are set out throughout the specification.

Detectable Moieties

Medical imaging techniques that rely on detection of emissions from tracers originating from within the body of the subject being imaged are widely used for diagnosis of various diseases. Nuclear physics-based molecular imaging techniques, such as positron emission tomography (PET) and single photon emission computed tomography (SPECT) allow functional imaging of subjects at the molecular level based on the use of radioactive isotopes. For example, SPECT is based on the use of radioisotopes that emit gamma rays and PET is based on the use of radioisotopes that emit positrons, which annihilate to produce gamma rays.

One of ordinary skill in the art will recognize that different radiopharmaceuticals display different pharmacokinetic properties, such as elimination, clearance from and/or accumulation in biological tissues, and half-life ($T_{1/2}$). Commercially available radiopharmaceuticals are widely used and may be appended onto biologically relevant molecules by chemical synthesis techniques well known in the art. Typically, the half-lives of radiotracers used in imaging are relatively short, and thus many cyclotrons are key features of radiotracer detection apparatuses, such as PET and SPECT scanners, or gamma cameras. Exemplary radionuclides that can be used as detectable moieties, include, but are not limited to, technetium (e.g., $^{99m}Tc$), indium (e.g., $^{111}In$), cobalt (e.g., $^{57}Co$), chromium (e.g., $^{51}Cr$), thallium (e.g., $^{201}Tl$), gallium (e.g., $^{67}Ga$), iodine (e.g., $^{123}I$, $^{125}I$, $^{131}I$) lutetium (e.g., $^{177}Lu$), and samarium (e.g., $^{153}Sm$). Any combination of the aforesaid radionuclides, or nuclear isomers thereof, can be used as a first and second detectable moiety. In embodiments, the combinations are suitable for dual-isotope imagine, e.g., SPECT imaging. Exemplary combinations include, but are not limited to, technetium (e.g., $^{99m}Tc$) and thallium (e.g., $^{201}Tl$), indium (e.g., $^{111}In$) and lutetium (e.g., $^{177}Lu$), technetium (e.g., $^{99m}Tc$) and indium (e.g., $^{111}In$) and technetium (e.g., $^{99m}Tc$) and iodine (e.g., $^{123}I$), or a nuclear isomer thereof.

Nuclear probes that may be used in accordance with the present invention may comprise single-photon gamma emitters or positron emitters. There are many single-photon gamma emitters in the range of 50 to 300 keV. Numerous FDA approved radiopharmaceuticals employ these radioisotopes.

It will be appreciated that provided radiopharmaceuticals may be administered singularly, or in combination with one or more radiopharmaceuticals. For example, administration of a combination of radiopharmaceuticals, e.g., two or more radiopharmaceuticals, may permit assessment, e.g., visualization, measurement, of two or more parameters of neuromuscular status. For example, in some embodiments, plasma membrane function and mitochondrial function may be assessed in combination by administration of two separate radiopharmaceuticals, each of which may be separately used to measure plasma membrane or mitochondrial function.

Indicators of Mitochondrial Function $^{99m}Tc$ is a generator-produced nuclide with a $T_{1/2}=6$ hours. $^{99m}Tc$ yields relatively high energy photons which can easily penetrate body tissues (140 keV g-rays). $^{99m}Tc$ is characterized by a relatively low radiation dose per mCi, so a patient can generally receive a maximum of 40-50 mCi, e.g., for a stress/rest study. $^{99m}Tc$-Sestamibi, $^{99m}Tc$-Tetrofosmin, and $^{99m}Tc$-Teboroxime have been approved as commercial radiopharmaceuticals, e.g., for myocardial perfusion imaging in nuclear cardiology (Kim, et al. World J Hepatol 2(1):21-31, 2010). These cationic $^{99m}Tc$ radiotracers are highly lipophilic with cationic or neutral charge, contain at least two ether-like linkages (N—O—R or C—O—R), and are excreted though the hepatobiliary system due to their high lipophilicity (Kim, et al. World J Hepatol 2(1):21-31, 2010).

$^{99m}Tc$-Sestamibi is a lipophilic, positively charged agent consisting of the $^{99m}Tc$ (technetium) isotope chelated within the Sestamibi molecular cage. $^{99m}Tc$-Sestamibi passes through cell membranes and accumulates in the highly electronegative environment of working muscle mitochondria. Changes in mitochondrial membrane potential thus dictate the overall accumulation of $^{99m}Tc$-Sestamibi in muscle cells as long as tissue perfusion is intact. $^{99m}Tc$-Sestamibi is characterized by high extraction efficiency, long biological half-life (imaging can be performed, e.g., up to 6 hours post injection), ease of preparation, and stability (e.g., stable for 6 hours).

$^{99m}Tc$ tetrofosmin includes the $^{99m}Tc$ (technetium) isotope chelated by two 1,2-bis[di-(2-ethoxyethyl)phopshino] ethane ligands which belong to the group of diphophies and which are referred to as tetrofosmin. $^{99m}Tc$ tetrofosmin is characterized by high extraction efficiency, long biological half-life (imaging can be performed, e.g., up to 6 hours post injection), ease of preparation, and stability (e.g., stable for 6 hours).

$^{99m}Tc$-Teboroxime is a tracer that is characterized by high myocardial extraction fraction, which is well correlated with the coronary blood flow, and the extremely rapid myocardial washout. In the case of cardiac imaging, this makes it necessary to complete the image collection shortly after the injection or to perform repeated scans by renewed Tc-99m-teboroxime administrations (Bisi, et al. G Ital Cardiol 22(7): 795-805, 1992). $^{99m}Tc$-Teboroxime is a neutral lipophilic agent characterized by high extraction efficiency, short biological half-life (imaging must be performed, e.g., within 25 minutes post injection), rapid myocardial clearance, ease of preparation, and stability (e.g., stable for 6 hours).

It will be appreciated that provided mitochondrial function agents may include any agent that permits assessment of mitochondrial function. Further examples of mitochondrial function agents include, but are not limited to, fatty acids and/or modified fatty acids. In general, a fatty acid is a carboxylic acid with a long aliphatic tail, which is either saturated (e.g., caprylic acid, capric acid, lauric acid, myristic acid, palmitic acid, stearic acid, arachidic acid, behenic acid, lignocercic acid, or cerotic acid) or unsaturated (e.g., myristoleic acid, palmitoleic acid, sapienic acid, oleic acid, elaidic acid, vaccenic acid, linoleic acid, linoelaidic acid, alpha-linolenic acid, arachidonic acid, eicosapentaenoic acid, erucic acid, or docosahexaenoic acid). Fatty acids are generally derived from triglycerides or phospholipids. Most naturally occurring fatty acids have a chain of an even number of carbon atoms, ranging from 4 to 28.

Fatty acids may be modified, e.g., to alter biological properties of the fatty acid. As used herein, the term "modified fatty acid" can be regarded as a synthetic or naturally occurring fatty acid that has been synthetically modified. In some embodiments, an organic substituent, e.g., an organic chemical structure, is bonded to the fatty acid to decreasing the in vivo rate of β-oxidation of the fatty acid in tissues of interest.

Indicators of Ionic Metabolism

Potassium plays a variety of roles in the body, including facilitation of nerve impulse conduction and the contraction of skeletal and smooth muscles, including the heart muscle. It also facilitates cell membrane function and proper enzyme activity. Proper function of potassium pumps is an important indicator of cell membrane function. Indeed, potassium leakage from cells is an indicator of impaired cell membrane function and necrosis, for example in myocardial cells (Gould, et al. *J Nucl. Med.* 32(1):1-9, 1991). Imaging methods utilizing potassium analogs provide information, e.g., quantitative information, about the status of plasma membrane function and/or viability of cells. Various potassium analogs may be used as $^{81}$Rb salts, $^{82}$Rb salts, $^{199}$Tl salts, $^{201}$Tl salts, and $^{13}$N ammonium ions. Tl$^+$, Cs$^+$, and Rb$^+$ behave like K$^+$ in that they are monovalent cations having an ionic radius, charge, and charge distribution very similar to that of K$^+$.

$^{201}$Tl is a low energy (71-80 keV X-rays from Hg-201 daughter)radioactive potassium analog. It functions as a perfusion marker under most conditions, e.g., in the $^{201}$Tl—Cl chemical form. For example, when administered, e.g., injected intravenously, $^{201}$Tl—Cl accumulates rapidly within the cells of several organs. Uptake of the $^{201}$Tl reflects both regional perfusion and sodium/potassium pump activity although ion channels and carriers may also play a role in tissue uptake. $^{201}$Tl is a cyclotron produced nuclide with a $T_{1/2}$=73 hours. $^{201}$Tl photons are easily attenuated by body tissues (71 keV Hg X-rays). In general, the long physical and biological half life of $^{201}$Tl increases radiation doses to patients, so patient injectable doses are generally limited to 5 mCi.

Neuromuscular Modulators/Agents

Provided methods can include administration of detectable moieties under conditions of rest, stress induced by exercise, stress induced by electrical stimulation, disease states, and/or pharmacological agents.

In some embodiments, a subject is subjected to stress conditions, e.g., physical exercise and/or electrical stimulation. For example, a radiopharmaceutical may be administered to a subject, prior to, during or after, being subjected to stress conditions. In some embodiments, a radiopharmaceutical is administered to a subject, who then is subjected to stress conditions, such as exercise, e.g., on a treadmill, or electrical stimulation of one or more muscles to simulate stress conditions.

Neuromuscular stimulation can include one or more of: an electrical stimulation, stimulation by a physical activity, or by administration of a neuromuscular stimulating agent.

In some embodiments, the neuromuscular stimulation is, or comprises, administration (e.g., systemic or local administration) of a neuromuscular stimulating agent, e.g., an agent that enhances or activates neuromuscular activity pre-synaptically, post-synaptically, or both. In one embodiment, the neuromuscular stimulating agent is a cholinesterase inhibitor, e.g., an acetylcholinesterase inhibitor. For example, a cholinesterase inhibitor chosen from one or more of ambenonium, ambenonium chloride, demecarium, demecarium bromide, echothiophate iodide, edrophonium, edrophonium chloride, neostigmine, neostigmine bromide, neostigmine methylsulfate, physostigmine, physostigmine salicylate, pyridostigmine, or pyridostigmine bromide. In one embodiment, the neuromuscular stimulating agent is an acetylcholinesterase inhibitor, e.g., edrophonium or edrophonium chloride.

In other embodiments, the subject is exposed to neuromuscular inhibition. Neuromuscular inhibition can be effected by administration (e.g., local or systemic administration) of an agent that reduces or inhibits neuromuscular activity pre-synaptically, post-synaptically, or both. In some embodiments, the agent is a neuromuscular blocking agent (e.g., a toxin (e.g., alpha-bungarotoxin)) or a ganglionic blocking drug (e.g., dicholine esters (e.g., succinylcholine), benzylisoquinolines (d-tubocurarine, atracurium, doxacurium, mivacurium) and pipecuronium, rocuronium, vecuronium), hexamethonium, trimethaphan, and mecamylamine. In other embodiments, the neuromuscular blocking agent is an anesthetic agent, including but not limited to, a ketamine; an opioid analgesic such as alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, and tramadol; a nonopioid analgesic such as apazone, etodolac, diphenpyramide, indomethacine, meclofenamate, mefenamic acid, oxaprozin, phenylbutazone, piroxicam, and tolmetin.

Detection

Several techniques can be used to detect the agents described herein. Examples of such techniques include single photon emission computed tomography (SPECT), Positron Emission Tomography (PET), Magnetic Resonance Imaging (MRI) and scintigraphy.

SPECT

Isotopes that decay by electron capture and/or γ emissions can be directly detected by SPECT. Certain proton-rich radionuclides, such as $^{123}$I and $^{99m}$Tc, may instead capture an orbiting electron, once again transforming a proton to a neutron (Sorenson J A, and Phelps M E. Philadelphia: W. B. Saunders; 1987). The resulting daughter nucleus often remains residually excited. This meta-stable arrangement subsequently dissipates, thereby achieving a ground state and producing a single γ photon in the process. Because γ photons are emitted directly from the site of decay, no comparable theoretical limit on spatial resolution exists for SPECT. However, instead of coincidence detection, SPECT utilizes a technique known as collimation (Jaszczak R J. Boca Raton: CRC Press; (1991): 93-118). A collimator may be thought of as a lead block containing many tiny holes that is interposed between the subject and the radiation detector. Given knowledge of the orientation of a collimator's holes, the original path of a detected photon is linearly extrapolated and the image is reconstructed by computer-assisted tomography.

Simultaneous dual-radionuclide studies can be performed with SPECT. SPECT permits identification of isotopes based on the energies of emitted photons, which allows for simultaneous dual-isotope imaging where distributions of the two isotopes are differentiated by setting multiple energy windows during image acquisitions (Shcherbinin, et al. *Phys. Med. Biol.* 57:4755-4769, 2012). However, the separation of tracers in positron emission tomography (PET) is more difficult because the annihilation photons created by the PET radiotracers always have the same energy (Rahmim, et al., *Nucl. Med. Commun.* 29:193-207, 2008).

Quantitative dual-isotope SPECT imaging is a useful tool that can be used to quantify and compare the biodistribution of different ligands, each labeled with a different radionuclide, in the same animal. Since the biodistribution results are not blurred by experimental or physiological inter-animal variations, this approach allows determination of each of the ligand's net targeting effect. However, dual-isotope quantification may potentially be complicated by crosstalk between the two radionuclides used. (Hinjen, et al. *Contrast Media Mol Imaging* 7(2):214-22, 2012) Various quantitative dual-isotope SPECT protocols have been developed to combine different radionuclides in the same animal, including, but not limited to: $^{99m}$Tc and $^{201}$Tl (de Jong, et al., *Eur. J. Nucl. Med. Mol. Imag.* 29:1063-71, 2002; Kadrmas, et al., *Phys. Med. Biol.* 44:1843-60, 1999; Song, et al., *IEEE Trans. Nucl. Sci.* 51:72-9, 2004); $^{111}$In and $^{177}$Lu (Hijnen, et al., *Contrast Media Mol Imaging,* 7(2):214-22, 2012); $^{111}$In and $^{99m}$Tc (James Brice, Dual-isotope SPECT/CT finds infections in diabetic feet. Diagnostic Imaging, Jan. 1, 2009; Du, et al., *J. Nucl. Med.* 49 (Suppl. 1):152, 2008); $^{123}$I and $^{99m}$Tc (Shcherbinin, et al. *Phys. Med. Biol.* 57:4755-4769, 2012; Ouyang, et al. *Med. Phys.* 34:3263-72, 2007; Ouyang, et al., *Med. Phys.* 36:602-11, 2009; Du, et al., *Med. Phys.* 34:3530-43, 2007; Du, et al., *Med. Phys.* 36:2021-33, 2009).

There are several advantages to dual-isotope SPECT analysis as compared to single isotope SPECT analysis. In some cases, a higher statistical relevance may be achieved with dual isotope imaging as compared to single isotope imaging. For example, Hinjen, et al. found that to achieve the same statistical relevance, seven animals were required in case of a single isotope test design as compared with only three animals when a dual-isotope test was used. Furthermore, an important advantage of dual energy SPECT scans is to eliminate mis-registration that frequently occurs when two scans are performed separately (Brice, Dual-isotope SPECT/CT finds infections in diabetic feet. Diagnostic Imaging, Jan. 1, 2009). It is also possible to combine the SPECT scan with a CT portion which provides additional anatomic landmarks for the physiologic images (Brice, Dual-isotope SPECT/CT finds infections in diabetic feet. Diagnostic Imaging, Jan. 1, 2009). For many imaging applications, the precise location of radioisotope targeting is important for accurate diagnosis and treatment of the patient. Additional advantages include the ability to perform multi-functional analyses, as well as increased patient comfort and throughput (Shcherbinin, et al. *Phys. Med. Biol.* 57:4755-4769, 2012).

Positron Emission Tomography (PET)

Positron Emission Tomography (PET) is a nuclear medicine imaging technique that detects pairs of gamma rays emitted indirectly by a positron-emitting radionuclide to form a three-dimensional image. In some cases, three dimensional imaging and analysis is aided by a CT X-ray scan that may be performed on the patient during the same session in the same machine. The emitted positrons from the decaying radioisotope travel in tissue of the subject for a short distance, during which time the positrons lose kinetic energy. The positrons decelerate to a point where they are able to interact with an electron, which annihilates both electron and positron, producing a pair of annihilation (gamma) photons moving in opposite directions. The photons are detected by a scintillator in the PET device. Statistical analysis and image reconstruction are performed in order to generate a three dimensional image of the tissue.

Magnetic Resonance Imaging (MRI)

Magnetic Resonance Imaging (MRI) is a medical technique using nuclear magnetic resonance to image nuclei of atoms inside the body. An MRI scanner has a large, powerful magnet where the magnetic field is used to align the magnetization of atomic nuclei in the body, and radio frequency magnetic fields are applied to systematically alter the alignment of the magnetization, causing the nuclei to produce a rotating magnetic field detectable by the scanner. Magnetic field gradients in different directions permit two dimensional images or three dimensional volumes to be obtained. Unlike other imaging techniques, such as CT scans or X-rays, MRI does not use ionizing radiation.

Scintigraphy

Scintigraphy is a diagnostic test used in nuclear medicine in which a radiopharmaceutical agent is administered to a subject, and the emitted radiation of captured by external detectors, e.g., gamma cameras, to form two-dimensional images. Scinitgraphy analyses can be performed on various tissues and regions of the body, including, but not limited to, biliary system, lungs, bone, heart, parathyroid, thryroid, and full body. Scintigraphy differs from SPECT and PET, which each form 3-dimensional images.

Diseases

Provided herein are efficient, quantitative assays and methods, as well as compositions and kits for assessing the neuromuscular status in a subject. The invention can be used, for example, for one or more of: (i) diagnosing, prognosing and/or evaluating, a subject (e.g., a subject having a neuronal and/or skeletal muscular disorders or conditions, including but not limited to, a muscle disorder, a motor neuron disease (e.g., Spinal Muscular Atrophy (SMA), Amyotrophic Lateral Sclerosis (ALS), neuropathy, myasthenia gravis, toxic syndromes, traumatic nerve injury, or a metabolic muscle disease); (ii) evaluating responsiveness to, or monitoring, a therapy; (iii) identifying a patient as being stable, showing improvement or showing disease progression; (iv) stratifying a subject; and/or (vi) more effectively monitoring, treating, or preventing a neuronal and/or muscular disorders or conditions.

"Treat," "treatment," and other forms of this word refer to the administration of a therapy (e.g., an ALS therapy), alone or in combination with one or more symptom management agents, to a subject, to impede progression of, to induce remission, to restore function, to extend the expected survival time of the subject and or reduce the need for medical interventions (e.g., hospitalizations). In those subjects, treatment can include, but is not limited to, inhibiting or reducing one or more symptoms; reducing relapse rate; prolonging survival, or prolonging progression-free survival, and/or enhanced quality of life and improving established disability.

As used herein, unless otherwise specified, the terms "prevent," "preventing" and "prevention" contemplate an action that occurs before a subject begins to suffer from the a multiple sclerosis relapse or progression and/or which inhibits or reduces the severity of the disease.

As used herein, and unless otherwise specified, a "therapeutically effective amount" of a compound is an amount sufficient to provide a therapeutic benefit in the treatment or management of the disease, or to delay or minimize one or more symptoms associated with the disease. A therapeutically effective amount of a compound means an amount of therapeutic agent, alone or in combination with other therapeutic agents, which provides a therapeutic benefit in the treatment or management of the disease. The term "therapeutically effective amount" can encompass an amount that improves overall therapy, reduces or avoids symptoms or causes of the disease, or enhances the therapeutic efficacy of another therapeutic agent.

As used herein, and unless otherwise specified, a "prophylactically effective amount" of a compound is an amount sufficient to prevent relapse of, or one or more symptoms associated with the disease, or prevent its recurrence. A prophylactically effective amount of a compound means an amount of the compound, alone or in combination with other therapeutic agents, which provides a prophylactic benefit in the prevention of a disease. The term "prophylactically effective amount" can encompass an amount that improves overall prophylaxis or enhances the prophylactic efficacy of another prophylactic agent.

Amyotrophic Lateral Sclerosis (ALS)

Amyotrophic Lateral Sclerosis (ALS), also known as Lou Gehrig's disease, is characterized by rapidly progressing weakness, muscle atrophy and fasciculations, muscle spasticity, difficulty speaking (dysarthria), difficulty swallowing (dysphagia), and difficulty breathing (dyspnea). The order and rate of symptoms of ALS varies from person to person, but ultimately most patients lose the ability to walk or use their hands and arms, and breathing and eating problems lead to pneumonia and weight loss. The rate of ALS progression can be measured using a standard outcome measure "ALS Functional Rating Scale (Revised)." In approximately 95% of ALS cases, no family history of the disease is present and there is no known cause for the disease. In familial ALS, genetic abnormalities have been identified, such as mutations in the superoxide dismutase (SOD1) gene. Mutations in several genes have been linked to various types of ALS. Pathophysiologically, ALS is characterized by death of both upper and lower motor neurons in the motor cortex of the brain, the brain stem, and the spinal cord. Prior to the destruction of motor neurons, they develop proteinaceous inclusions in their cell bodies and axons.

ALS diagnosis is usually not definitive, and generally requires a neurologic examination at regular intervals to confirm a diagnosis. Tests that are generally performed in order to exclude the possibility of a condition other than ALS include electromyography (EMG), nerve conduction velocity (NCV), magnetic resonance imaging (MRI), blood tests, and urine tests, among others.

Current therapies for ALS are limited, and most current therapies are designed to relieve symptoms and improve quality of life for patients. For example, Riluzole (Rilutek) is a treatment that has been found to improve survival, however, only to a modest extent. Several drugs are currently in clinical trials, including thalidomide, lenalidomide, and dexpramipexole (KNS-760704). Exemplary symptom management treatments for ALS include, but are not limited to, medications to reduce fatigue, ease muscle cramps, control spasticity (e.g., spasmolytic (anti-spastic) agents, such as baclofen, diazepam, tizanidine, and dantrolene), reduce excess saliva and phlegm, alleviate pain, depression, sleep disturbances, dysphagia (e.g., trihexyphenidyl, amitriptyline), and constipation.

EXAMPLES

Example 1

Test for Neuromuscular Health Status Using Simultaneous $^{99m}$Tc-Sestamibi and $^{201}$Tl—Cl Imaging This example describes an imaging approach for assessing skeletal muscle health by administering $^{99m}$Tc-Sestamibi and $^{201}$Tl—Cl both in a single intravenous injection and then simultaneously detecting their accumulation into skeletal muscle through SPECT imaging via distinct radiation energy windows, which are specific for each isotope. Through this approach, each imaging agent alone, as well as the change in uptake of one agent relative to the other, was measured, permitting evaluation of multiple physiological processes in muscle simultaneously.

Imaging agents ($^{99m}$Tc-Sestamibi and $^{201}$Tl-Chloride) were ordered from commercial radiopharmacies for calibration and delivery on each day of SPECT imaging. Imaging agents were administered by intravenous injection in the lateral tail-vein. Animals were returned to their cages after injection for the distribution period or placed directly on the imaging system for SPECT acquisition, depending on the imaging protocol and desired time-points. For the imaging session, subjects were anesthetized using a gas mixture of isoflurane and oxygen. In-vivo SPECT and CT data were acquired using the NanoSPECT/CT® (Bioscan, Washington, D.C.), a dual modality imaging system that combines a 4-headed SPECT camera with a computed tomography (CT) acquisition system on the same axis of rotation. During imaging, subjects were placed on a heated bed with integrated anesthesia delivery and bed heating. The animals' body temperatures were maintained at 36 to 37° C. for the duration of image acquisition. Each imaging time-point included three scans: a planar x-ray scout scan, an x-ray CT scan for anatomical reference (6-9 min., 45-65 KVp, 180 angular projections per FOV), and a SPECT scan (20-90 min., 20 angular projections per FOV). SPECT data were reconstructed using the HiSPECT processing module (Scivis GmbH, Gottingen, Germany). An iterative, ordered subsets expectation-maximization (OSEM) algorithm for multiplexed, multi-pinhole SPECT was used for reconstruction. Reconstructed images from the NanoSPECT/CT® were generated in units of activity per volume. Namely, the values assigned to the voxels (volume elements) comprising the 3D reconstructed SPECT images were in units of μCi/mm3 or equivalent. Uptake and concentration of radiotracer were quantified in select regions-of-interest (ROI) using the VivoQuant™ post-processing suite.

Figure 2:
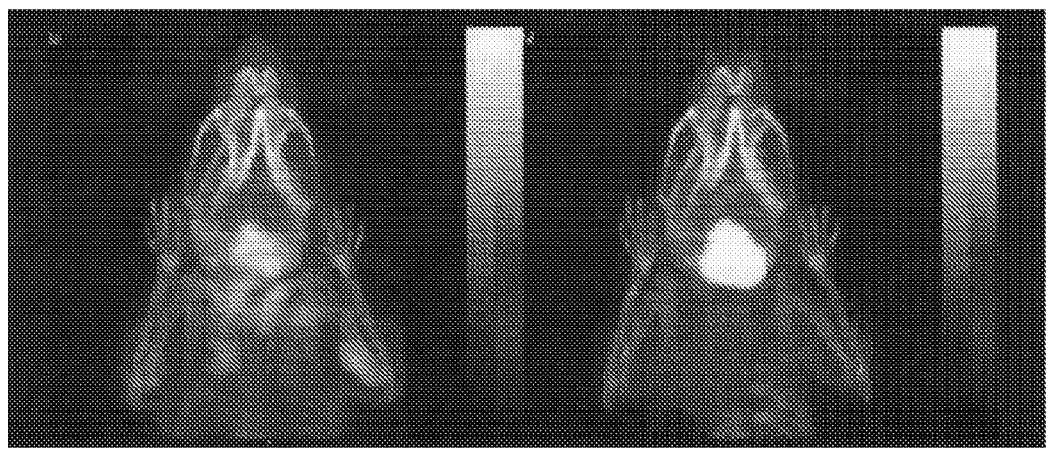
FIG. 2 depicts exemplary images of skeletal muscle uptake, acquired in vivo at 3 hours post-injection of $^{99m}$Tc-Sestamibi and $^{201}$Tl—Cl radiopharmaceuticals.

FIG. 1 depicts images from a dual radiotracer imaging approach in a mouse and a rat. While a high signal was observed in several organs due to hepatic and renal clearance as well as thyroid and salivary gland uptake, a consistent retention of both agents was observed in muscle. Muscle accumulation of $^{201}$Tl—Cl was more widespread than was $^{99m}$Tc-Sestamibi and there was some interspecies difference in the extent and relative uptake of the two probes. FIG. 2 shows a close-up of the upper torso in a mouse and highlights the accumulated signal in the musculature of the arms, shoulders and back.

Unlike man, imaging studies in animals generally require the use of short acting general anesthesia in order to place the animal in the imaging camera for acquiring an image while avoiding movement. However, general anesthesia perturbs function of excitable biological membranes and could therefore affect imaging results with $^{99m}$Tc-Sestamibi and $^{201}$Tl—Cl. Therefore, our experimental paradigm involved the i.v. administration of $^{99m}$Tc-Sestamibi and $^{201}$Tl—Cl to briefly-anesthetized animals, followed by an awake uptake period, and then only brief use of short acting isoflurane anesthesia for the imaging period. The data in FIGS. 1 and 2 thus represent injection of isotopes at time zero with imaging of their distribution 3 hours later under short acting anesthesia. This approach allowed the imaging agents to be trapped in muscle prior to anesthesia and thereby to reflect the ongoing neuromuscular activity of the 3 hours period prior to imaging.

Figure 3:
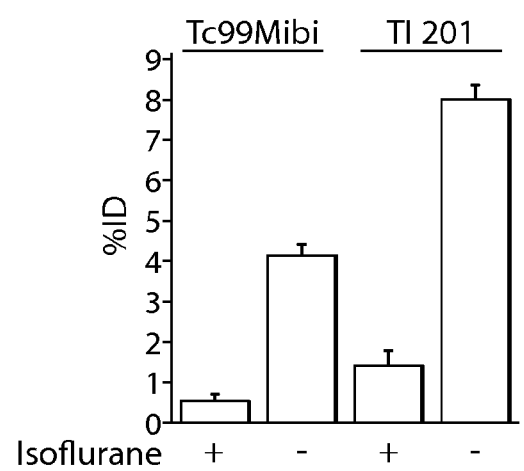
FIG. 3 depicts an exemplary comparison of radiopharmaceutical uptake into skeletal muscle of both legs between two imaging paradigms. The first group (+) remained under anesthesia for a 30-minute uptake period prior to imaging. The second group (-) remained awake during a 30-minute uptake period prior to imaging. Image acquisition was performed under anesthesia in both groups.

This need for imaging under anesthesia in animals is not necessary in human imaging studies. However, we took advantage of the inhibitory effect of anesthesia on neuronal and muscle function to assess its impact on our imaging assay. In order to directly assess the effect of general anesthesia on muscle uptake of the two radiopharmaceutical agents, we imaged animals 30 minutes following i.v. administration of $^{99m}$Tc-Sestamibi and $^{201}$Tl—Cl. In one set of animals ('+,' n=3) we applied isoflurane anesthesia at the time of $^{99m}$Tc-Sestamibi and $^{201}$Tl—Cl injection and maintained the anesthesia throughout the 30 minute radiolabel uptake-period as well as for the duration of image acquisition. In comparison, in a second group of animals ('−,' n=9), we applied isoflurane anesthesia briefly (3-5 min) for the intravenous injection of both radiopharmaceutical agents and then allowed the subjects to wake up for the 30 minute uptake period prior to imaging. FIG. 3 shows that continuous isoflurane anesthesia inhibited the accumulation of both agents into muscle. Quantitative units of radioactivity per volume was expressed as uptake: percent injected dose (% ID), activity (mCi, kBq). The percent of injected dose accumulated into the muscles of the right and left legs are shown.

Example 2

Test for Neuromuscular Health Status Using Simultaneous $^{99m}$Tc-Sestamibi and $^{201}$Tl—Cl Imaging with Neuromuscular Stimulation By introducing pharmacological, metabolic, or electrical stimulation challenges into the imaging paradigm, our approach allows for selective exploration of additional distinct physiological processes acting on muscle. This example demonstrates that an enhancement of uptake of imaging agents into muscle can be achieved with use of techniques that stimulate neuromuscular synaptic transmission. Pharmacological agents such as acetylcholinesterase inhibitors enhance acetylcholine synaptic transmission at the neuromuscular junction, thereby stimulating muscle plasma membrane ionic fluxes and muscle contraction. Electrical stimulation of specific motor nerves also enhances neuromuscular transmission and contraction of the respectively innervated muscles. The ability of muscle metabolism to be stimulated by acetylcholinesterase inhibitors or nerve stimulation requires intact healthy presynaptic motor nerve endings and intact postsynaptic acetylcholine receptors. By coupling such pharmacological and electrical stimulation paradigms with the dual $^{99m}$Tc-Sestamibi and $^{201}$Tl—Cl imaging paradigm described in Example 1, we have developed a convenient approach for early evaluation of several neuromuscular disorders such as motor neuron disease (SMA, ALS), neuropathies, myasthenia gravis, and a variety of toxic syndromes. Likewise, metabolic challenges with agents that stimulate muscle bioenergetics activity can also be applied to our imaging paradigm to evaluate metabolic muscle diseases.

In order to assess the action of neuromuscular stimulation on $^{99m}$Tc-Sestamibi and $^{201}$Tl—Cl uptake into muscle we used the acetylcholinesterase inhibitor edrophonium (0.2 mg/kg, i.v.) to enhance ongoing neuromuscular synaptic transmission. We used three different cohorts of animals (n=3). In one cohort we examined baseline neuromuscular activity by giving the $^{99m}$Tc-Sestamibi and $^{201}$Tl—Cl (listed as m/t in figure) at time zero and acquiring images under brief isoflurane anesthesia at 30 minutes post injection. Another cohort received edrophonium injection immediately following the m/t dosing but prior to the imaging under anesthesia. The last cohort received the edrophonium 30 minutes prior to the m/t dosing. This approach standardized the anesthesia and imaging phase of the experiment while making the edrophonium dose timing the only variable.

Figure 4:
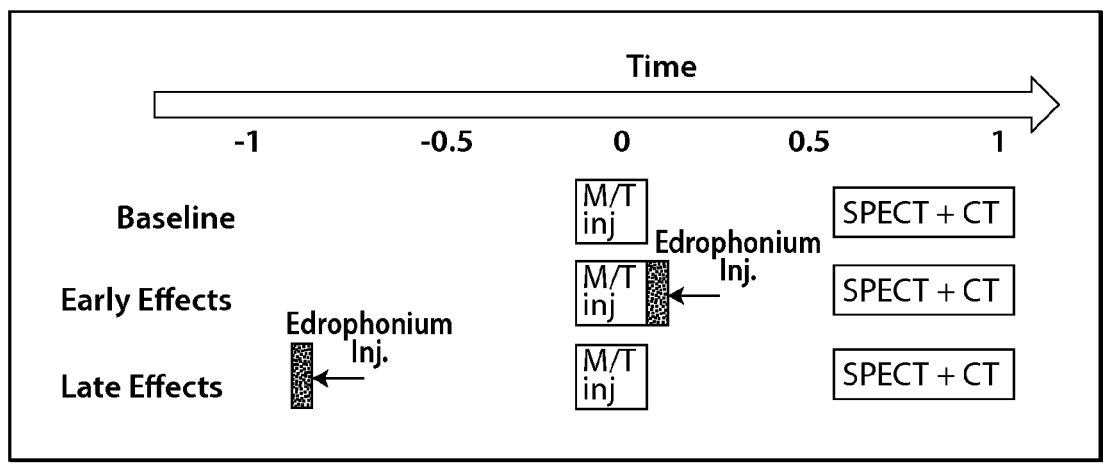
FIG. 4 is an exemplary schematic diagram depicting a timeline of an experiment assessing the impact of edrophonium on the pharmacokinetics of thallium and Mibi. Thallium and Mibi were imaged in three cohorts of rats (n=3 each): control/baseline; prior to injection of 0.2 mg/kg of edrophonium; following injection of 0.2 mg/kg of edrophonium. Whole-body SPECT/CT images were collected 30 minutes post-injection of the mixed Thallium/Mibi dose. The drugs gamma emissions of the radioisotopes ($^{99m}$Tc and $^{201}$Tl) were collected in separate energy windows, permitting simultaneous imaging of the relevant radiopharmaceuticals.
Figure 5:
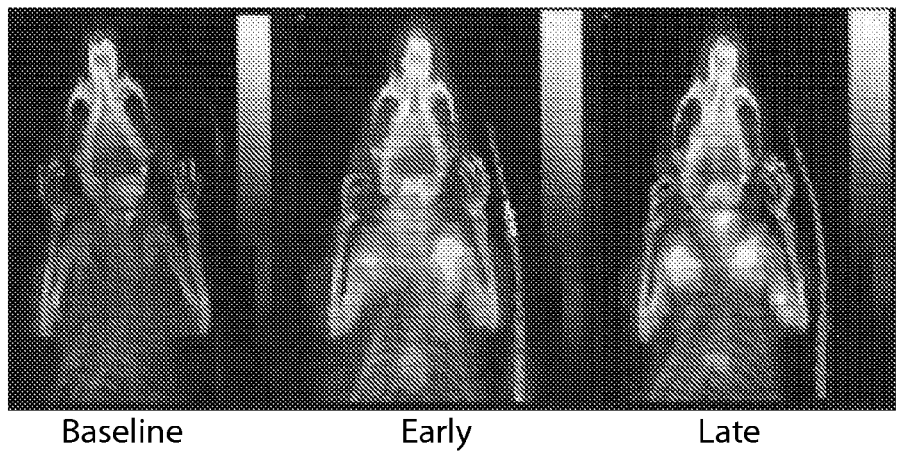
FIG. 5 depicts exemplary images of $^{201}$Tl—Cl without, post- and pre-edrophonium intervention. Thallium uptake was increased by the introduction of edrophonium in control rats as indicated qualitatively by "brighter" muscle uptake on a common scale.

FIG. 4 is an exemplary schematic diagram of an experiment assessing the impact of edrophonium on the pharmacokinetics of $^{99m}$Tc-Sestamibi and $^{201}$Tl—Cl. $^{99m}$Tc-Sestamibi and $^{201}$Tl—Cl were imaged in three cohorts of rats (n of 3 each): control/baseline; prior to injection of 0.2 mg/kg of edrophonium; following injection of 0.2 mg/kg of edrophonium. Whole body SPECT/CT images were collected 30 minutes post-injection of the mixed $^{99m}$Tc-Sestamibi and $^{201}$Tl—Cl dose. The drugs' gamma emissions of the radioisotopes ($^{99m}$Tc and $^{201}$Tl) were collected in separate energy windows, permitting simultaneous imaging of the relevant radiopharmaceuticals. FIG. 5 shows representative images of $^{201}$Tl—Cl without, post- and pre-edrophonium intervention. Thallium uptake was increased by the introduction of edrophonium in control rats as indicated qualitatively by brighter muscle uptake on a common scale. As compared to the baseline, both pre- and post-m/t dosing with edrophonium dramatically enhanced $^{201}$Tl uptake into muscle.

Figure 6:
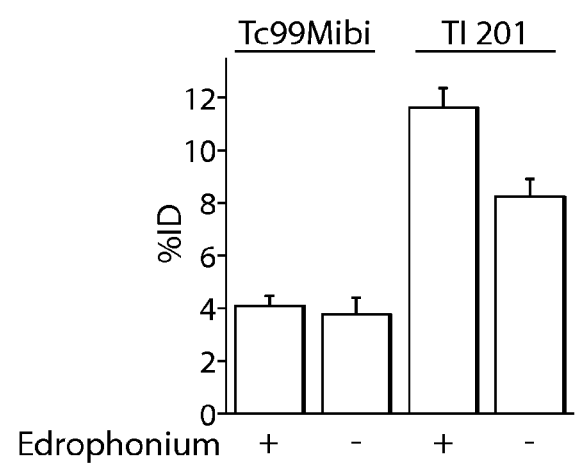
FIG. 6 depicts an exemplary comparison of radiopharmaceutical uptake in skeletal muscle between two imaging paradigms. The first group (+) represents subjects that received an edrophonium injection (i.v.) immediately after radiotracer administration. The second group (-) represents subjects that did not receive edrophonium after radiotracer injection. All other aspects of data collection were identical between the two groups.

However, either pre- or post-m/t, edrophonium dosing had no effect on $^{99m}$Tc-Sestamibi uptake into muscle. FIG. 6 depicts comparison of radiopharmaceutical uptake in skeletal muscle between two imaging paradigms. The '+' represents subjects that received an edrophonium injection (i.v.) immediately after radiotracer administration. The '−' represents subjects that did not receive edrophonium after radiotracer injection. All other aspects of data collection were identical between the '+' and '−' scenarios. Quantitative units of radioactivity per volume was expressed as uptake: percent injected dose (% ID), activity (mCi, kBq). As can be seen in FIG. 6, when we evaluated the effect of edrophonium statistically, a highly significant edrophonium effect was seen on $^{201}$Tl uptake but not on $^{99m}$Tc-Sestamibi.

The concentration of radioactivity was determined as follows: percent injected dose per gram (% ID/g), activity per volume (mCi/cc, kBq, etc.), nM concentration (requires a known specific activity of the injected compound, e.g. Ci/mol), SUV (standardized uptake value—concentration in the organ/region of interest normalized by 'injected dose/body weight').

Figure 7:
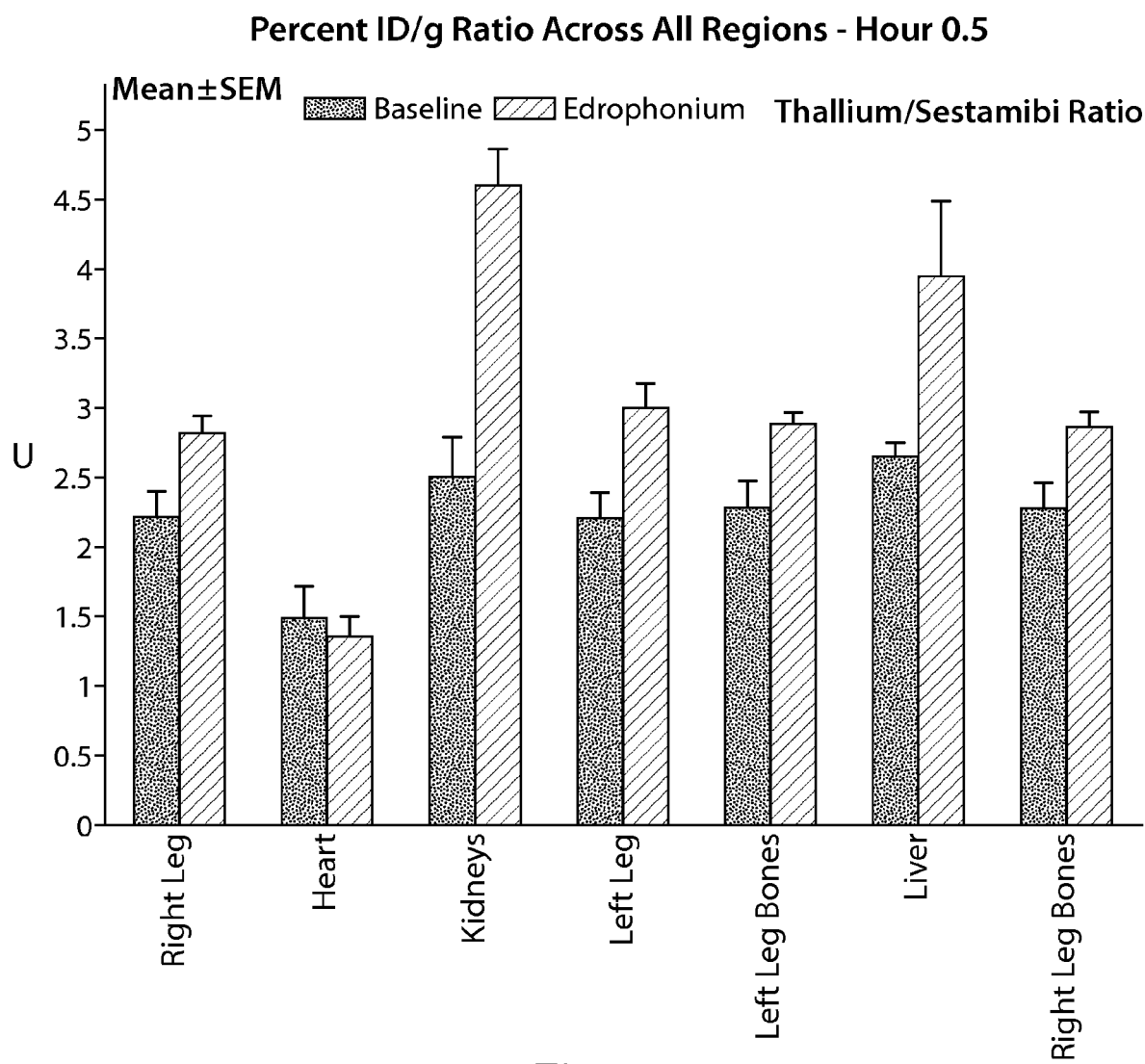
FIG. 7 depicts exemplary $^{201}$Tl: $^{99m}$Tc-Sestamibi ratios across all regions of animals treated with or without edrophonium. Images were acquired 30 minutes post administration of $^{99m}$Tc-Sestamibi, $^{201}$Tl, and edrophonium.

The ratio of $^{201}$Tl to $^{99m}$Tc-Sestamibi was determined as percent injected dose (% ID)/g. FIG. 7 provides exemplary $^{201}$Tl: $^{99m}$Tc-Sestamibi ratios across selected regions of animals treated with or without edrophonium. Images were acquired 30 minutes post administration of $^{99m}$Tc-Sestamibi, $^{201}$Tl, and edrophonium.

These data demonstrate that the effect of edrophonium on the uptake of each radiopharmaceutical agent is markedly different than the effects of isofluorane, suggesting that the provided approach can distinguish the actions of distinct stimuli and, by extension, disease status on muscle physiology.

INCORPORATION BY REFERENCE

The contents of all references, figures, sequence listing, patents and published patent applications cited throughout this application are hereby incorporated by reference. All publications, patents, and patent applications mentioned herein are hereby incorporated by reference in their entirety as if each individual publication, patent or patent application was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed.

Other embodiments are within the following claims.

What is claimed is:

1. A method for evaluating a neuromuscular status in a subject, comprising:
   administering to the subject a first and a second detectable agent, wherein:
   (i) the first detectable agent is an indicator of mitochondrial function or activity, wherein the first detectable agent includes at least one of $^{99m}$Tc-Sestamibi, $^{99m}$Tc-Tetrofosmin, and $^{99m}$Tc-Teboroxime, and
   (ii) the second detectable agent is an indicator of plasma membrane ionic metabolism, wherein the second detectable agent includes at least one of $^{127}$Cs salts, $^{129}$Cs salts, $^{81}$Rb salts, $^{82}$Rb salts, $^{199}$Tl salts, $^{201}$Tl salts, and $^{13}$N ammonium ions;
   detecting the first and second detectable agents disposed in a skeletal muscle cell or tissue in the subject;
   obtaining a reference value of the first detectable agent and a reference value of the second detectable agent; and
   comparing the detected first detectable agent and the detected second detectable agent to the respective reference value;
   wherein the first detectable agent and the second detectable agent are administered at a time and/or in an amount sufficient for each agent, or both agents, to be detected in the subject within a detection interval;
   wherein a change in one or more of the first detectable agent, the second detectable agent, or both, relative to the respective reference value is indicative of neuromuscular status, and wherein the first and second detectable agents are each detected after both agents have been administered; and
   wherein the reference value of the first detectable agent and the reference value of the second detectable agent is obtained from a healthy subject or a healthy group of subjects.

2. The method of claim 1, further comprising providing to the subject a neuromuscular stimulation in an amount or level such that one or more physiological processes in the skeletal muscle or tissue is/are stimulated.

3. The method of claim 2, wherein the neuromuscular stimulation comprises one or more of: electrical stimulation, stimulation with physical activity, or stimulation by a neuromuscular stimulating agent.

4. The method of claim 3, wherein the neuromuscular stimulation occurs prior to administration of one or both of the first and second detectable agents.

5. The method of claim 3, wherein the neuromuscular stimulation occurs after administration of one or both of the first and second detectable agents.

6. The method of claim 3, wherein the neuromuscular stimulation occurs concurrently with administration of one or both of the first and second detectable agents.

7. The method of claim 2, wherein the neuromuscular stimulation is or comprises administration of a neuromuscular stimulating agent.

8. The method of claim 1, wherein the first detectable agent distributes and/or localizes to the mitochondria in the skeletal muscle cell or tissue in the subject.

9. The method of claim 1, wherein the second detectable agent distributes and/or localizes to a perfused muscle cell or tissue.

10. The method of claim 1, wherein a level or amount of the second detectable agent is indicative of tissue perfusion and/or a function of one or more of: a sodium-potassium pump, an ion channel or an ion carrier in the skeletal muscle cell or tissue.

11. The method of claim 1, wherein the first and second detectable agents are suitable for dual-isotope SPECT imaging.

12. The method of claim 1, wherein the first and second detectable agents are administered to the subject concurrently.

13. The method of claim 1, wherein the first and second detectable agents are each detected during the detection interval.

14. A method for evaluating a subject, comprising determining a neuromuscular status value in the subject having a muscle disorder or a motor neuron disease, or at risk of developing the muscle disorder or a motor neuron disease by:
   performing the method of claim 1; and then
   determining a first ratio of the first detectable agent relative to the reference value of the first detectable agent and a second ratio of the second detectable agent relative to the reference value of the second detectable agent to determine the neuromuscular status value.

15. The method of claim 14, wherein the disease or disorder is Spinal Muscular Atrophy (SMA), Amyotrophic Lateral Sclerosis (ALS), neuropathy, myasthenia gravis, toxic syndromes, traumatic nerve injury, or a metabolic muscle disease.

16. The method of claim 14, wherein, responsive to a determination of said neuromuscular status value, the method further includes one or more of the following:
   (i) diagnosing and/or prognosing the subject as having the muscle disorder or the motor neuron disease;
   (ii) identifying the subject as being in need of a therapy;
   (iii) identifying the subject as having an increased or a decreased response to a therapy;
   (iv) monitoring disease progression in the subject; and/or
   (v) administering a therapy to the subject.

17. The method of claim 16, wherein one or more of (i)-(v) are effected in response to the neuromuscular status value, wherein a change in the neuromuscular status value relative to the reference value of the first detectable agent and/or a change in the neuromuscular status value relative to the reference value of the second detectable agent indicates one or more of:
   identifies the subject as being in need of the therapy; identifies the subject as having an increased or decreased response to the therapy; determines the treatment to be used; and/or
   determines or predicts the time course of the disease.

18. A method of treating a muscle disorder or a motor neuron disease in a subject having the disease or disorder, said method comprising:
   performing the method of claim 1 and then determining a neuromuscular status value by evaluating a change in the first detectable agent relative to the reference value of the first detectable agent or a change in the second detectable agent relative to the reference value of the second detectable agent, and responsive to a determination of the value of the neuromuscular status value, performing one, two or more of:

administering a therapy;

administering an altered dosing of a therapy;

administering or altering the schedule or time course of a therapy; or administering an alternative therapy, thereby treating the muscle disorder or motor neuron disease in the subject.

19. The method of claim 18, wherein the muscle disorder or motor neuron disease is Spinal Muscular Atrophy (SMA), Amyotrophic Lateral Sclerosis (ALS), neuropathy, myasthenia gravis, toxic syndromes, traumatic nerve injury, or a metabolic muscle disease.

\* \* \* \* \*